US009474597B2

(12) United States Patent
Accola (10) Patent No.: US 9,474,597 B2
(45) Date of Patent: Oct. 25, 2016

(54) PROSTHETIC HEART VALVES AND DEVICES, SYSTEMS AND METHODS FOR PROSTHETIC HEART VALVES

(76) Inventor: Kevin D. Accola, Orlando, FL (US)

( * ) Notice: Subject to any disclaimer, the term of this patent is extended or adjusted under 35 U.S.C. 154(b) by 691 days.

(21) Appl. No.: 13/811,451

(22) PCT Filed: Jul. 21, 2011

(86) PCT No.: PCT/US2011/044891
§ 371 (c)(1),
(2), (4) Date: May 31, 2013

(87) PCT Pub. No.: WO2012/012660
PCT Pub. Date: Jan. 26, 2012

(65) Prior Publication Data
US 2013/0261741 A1    Oct. 3, 2013

Related U.S. Application Data

(60) Provisional application No. 61/366,202, filed on Jul. 21, 2010.

(51) Int. Cl.
*A61F 2/24* (2006.01)
*A61B 17/12* (2006.01)

(52) U.S. Cl.
CPC ............ *A61F 2/24* (2013.01); *A61B 17/1204* (2013.01); *A61B 17/12136* (2013.01); *A61F 2/2403* (2013.01); *A61F 2/243* (2013.01); *A61F 2/2409* (2013.01); *A61F 2/2412* (2013.01); *A61F 2/2427* (2013.01)

(58) Field of Classification Search
CPC ...... A61F 2/24; A61F 2/2403; A61F 2/2409; A61F 2/2412; A61F 2/2418; A61F 2/2427; A61F 2/243
See application file for complete search history.

(56) References Cited

U.S. PATENT DOCUMENTS

| | | | |
|---|---|---|---|
| 6,248,121 B1* | 6/2001 | Nobles | A61B 17/12109 606/194 |
| 2001/0044656 A1* | 11/2001 | Williamson, IV | A61F 2/2427 623/2.11 |
| 2003/0109923 A1* | 6/2003 | Chinn | A61F 2/2409 623/2.17 |
| 2003/0125805 A1* | 7/2003 | Johnson | A61F 2/2412 623/2.11 |
| 2003/0149476 A1* | 8/2003 | Damm | A61F 2/2418 623/2.1 |
| 2004/0034380 A1* | 2/2004 | Woolfson | A61F 2/2427 606/170 |

(Continued)

OTHER PUBLICATIONS

International Search Report, WO2012012660; Mar. 20, 2012.

*Primary Examiner* — David C Eastwood
(74) *Attorney, Agent, or Firm* — Timothy H. Van Dyke; Beusse, Wolter, Sanks & Maire, PLLC (57) ABSTRACT

Described herein is a unique sutureless heart valve that includes a deployment mechanism having a plurality of fasteners. The plurality of fasteners may be actuated at least two states: a disengaged state wherein said plurality of fasteners are retracted, and an engaged state wherein said plurality of fasteners are extended; and further comprising a deployed state wherein said plurality of fasteners, when extended, are irreversibly locked such that said heart valve is securely deployed at the target surgical site. The valve deployment mechanism comprises a ring assembly comprising a first annular member onto which said plurality of fasteners are associated and a second annular member peripheral to said first annular member and comprising a series of windows through which individual fasteners of said plurality of fasteners project.

16 Claims, 10 Drawing Sheets

(56) References Cited

U.S. PATENT DOCUMENTS

| | | | | |
|---|---|---|---|---|
| 2004/0044406 | A1* | 3/2004 | Woolfson | A61F 2/2427 623/2.11 |
| 2005/0015112 | A1* | 1/2005 | Cohn | A61F 2/2412 606/200 |
| 2005/0033398 | A1* | 2/2005 | Seguin | A61B 17/072 623/1.11 |
| 2005/0107872 | A1* | 5/2005 | Mensah | A61L 27/16 623/2.14 |
| 2005/0137686 | A1* | 6/2005 | Salahieh | A61F 2/2418 623/2.11 |
| 2005/0137702 | A1* | 6/2005 | Haug | A61F 2/013 623/2.38 |
| 2006/0052867 | A1* | 3/2006 | Revuelta | A61F 2/2418 623/2.18 |
| 2006/0136054 | A1* | 6/2006 | Berg | A61F 2/2409 623/2.38 |
| 2006/0173524 | A1* | 8/2006 | Salahieh | A61F 2/2439 623/1.11 |
| 2008/0221672 | A1* | 9/2008 | Lamphere | A61F 2/2418 623/2.12 |
| 2008/0269877 | A1* | 10/2008 | Jenson | A61F 2/013 623/2.11 |
| 2009/0259306 | A1* | 10/2009 | Rowe | A61F 2/2418 623/2.12 |
| 2010/0249908 | A1* | 9/2010 | Chau | A61F 2/2418 623/1.26 |
| 2011/0060407 | A1* | 3/2011 | Ketai | A61B 17/00234 623/2.37 |
| 2011/0167603 | A1* | 7/2011 | Vesely | A61F 2/2427 29/221.6 |
| 2014/0277411 | A1* | 9/2014 | Bortlein | A61F 2/24 623/2.11 |
| 2014/0316519 | A1* | 10/2014 | Veseley | A61F 2/2427 623/2.11 |

* cited by examiner

FIGURE 5a (HOOK RETRACTED)

FIGURE 5b (HOOK EXTENDED)

FIGURE 5c (HOOK LOCKED)

PROSTHETIC HEART VALVES AND DEVICES, SYSTEMS AND METHODS FOR PROSTHETIC HEART VALVES

CROSS-REFERENCE TO RELATED APPLICATIONS

This application is related to U.S. Provisional Application No. 61/366,202 filed on Jul. 21, 2010, to which priority is claimed under 35 USC 119. The full disclosure of this application is incorporated herein in its entirety.

FIELD

Embodiments of this invention generally relate to prosthetics, devices, systems, and techniques used to treat various heart conditions.

BACKGROUND

The four chambers of the human heart are the right atrium, left atrium, right ventricle, and left ventricle. The heart has valves (mitral and tricuspid) between the atria and the ventricles and has valves (aortic and pulmonary) in the arteries leaving the heart. These heart valves generally maintain the unidirectional flow of blood by opening and closing depending on difference in pressure on each of their sides. Various heart conditions are treated by surgically replacing one or more of the heart's valves with bio-prosthetic (e.g., tissue-based valves from pigs, cows, etc.) or artificial prosthetic valves (e.g., metal, etc.). For example, such prosthetic valves are often surgically inserted to treat aortic stenosis. Aortic stenosis occurs where a normal aortic valve, which is generally circular with three leaflets that open or close a relatively large orifice, becomes stenatic over time such that its leaflets become calcified, the aortic valve cannot fully open, and the flow of blood is restricted.

A common method of treating aortic stenosis uses open-heart valve surgery that generally involves opening the chest, stopping the heart, opening the heart and sewing in a prosthetic valve with usually from fifteen to eighteen sutures to replace the stenatic valve. The stenatic valve's leaflets may be cut and some or all of the calcification cut away to allow more room for the inserted prosthetic valve. The prosthetic valve typically has a sewing ring or solid annulus through which the sutures are threaded during surgery. While sewing these sutures to secure a valve does not usually take a long time, the use of sutures generally requires a sternotomy, which is a procedure that typically involves a vertical incision along the breastbone, division or cracking of the breastbone itself, and results in long patient recovery periods. Without such a sternotomy, the surgeon's task of sewing in the sutures can be difficult and, for example, may involve the surgeon having to look and/or work through a small hole while inserting the sutures.

Various suture-less prosthetic valves have been used. Generally, however, fixative devices used with such prosthesis have been unsatisfactorily with respect to allowing the inserted valve to leak or move. Such failures make such valves more risky (e.g., in terms of patient mortality, etc.) than the valves deployed using suture-based techniques. Recently, for example, percutaneous valves have been deployed without sutures using a one-shot deployment technique that does not allow adjustment after deployment. For example, a catheter can be introduced across the valve, the valve dilated, positioned, and expanded, for example, with a nitinol (nickel titanium) support. As the valve expands, it is held in place. However, once the valve has been so deployed, it cannot be adjusted. The deployment is permanent until the valve is surgically removed, for example, by cutting it out and, thereafter, the same valve cannot be redeployed. If the percutaneous valve itself becomes calcified, removal can be hampered by its permanent deployment mechanisms and may result in the unwanted cracking of calcification that results in loose material in the heart.

SUMMARY

New prosthetic valves, prosthetic valve deployment systems, and techniques for prosthetic valve deployment and use are disclosed herein. In one exemplary deployment method, a surgeon makes a small incision rather than performing a sternotomy, cuts out the heart valve that is being replaced, positions a prosthetic valve within the heart using a deployment device, deploys and undeploys the prosthetic valve one or more times to ensure that the prosthetic valve is in an appropriate position and that calcification has been adequately removed, performs a final deployment of the valve in which the valve's deployment mechanism is locked into place, detaches the deployment device from the valve, and closes the heart and otherwise finishes the procedure. Features of certain of the prosthetic valves and/or the deployment systems disclosed herein allow prosthetic valves to be deployed with limited or no suture use and thus generally without requiring a sternotomy. Certain of the valve deployment systems and methods additionally or alternatively allow a valve to be engaged and disengaged one or more times to allow the surgeon to ensure that the position and fit of the valve is acceptable prior to more permanently deploying the valve. Many or all of the prosthetic valves and/or the deployment systems disclosed herein can be used to replace the aortic, mitral, tricuspid, or pulmonary valves. Thus, examples described in the context of aortic valve replacement are generally applicable to replacement of other valve types with modifications as may be appropriate given differences in valve size, orientation, or other attributes. A valve deployment system may also include an improved cannula system that combines a balloon occluder insufflator that prevents blood from returning and a cannula to administer cardioplegia, which is the high potassium solution used to stop the heart. Combining the cannula and occluder may reduce the number and/or size of surgical incisions required. These exemplary embodiments are mentioned not to limit or define the disclosure, but to provide examples of embodiments to aid understanding thereof. Embodiments are discussed in the Detailed Description, and further description is provided there. Advantages offered by the various embodiments may be further understood by examining this specification.

BRIEF DESCRIPTION OF THE DRAWINGS

Some embodiments are better understood by reading the following Detailed Description, taken together with the Drawings, wherein.

FIG. 5 shows a close-up side view (right column) and cross-section view (left column) of an annular ring embodiment with fasteners. The fasteners are shown retracted (FIG. 5a), extended (FIG. 5b) and locked (FIG. 5c).

FIG. 6a shows the cannula assembly out of subject and FIG. 6b shows the cannula assembly in the aorta of a subject.

FIG. 7 shows a top view of radially expandable member for use in conjunction with a heart valve embodiment. The radially expandable member is shown contracted (FIG. 7a) and expanded (FIG. 7b)

FIG. 8a-b shows a side view of the embodiment shown in FIG. 7.

FIG. 9a-c shows a full side view of an annular ring member embodiment corresponding to the close-up view shown in FIG. 5a-c.

FIG. 11a-f shows a sequential depiction of a surgical method involving deployment of a sutureless heart valve embodiment.

DETAILED DESCRIPTION

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

According to one embodiment, the invention is directed to a sutureless heart valve for use in heart valve replacement, or repair surgery at a target surgical site. The sutureless heart valve typically includes a valve component having two or more cusps, typically three cusps; and a unique valve deployment mechanism. The deployment mechanism is typically integrated with or attached to the valve component in an outward orientation. In a specific embodiment the valve deployment mechanism is made up of generally annular components that define a central cavity. In this specific embodiment, the valve component rests, at least partially, in this cavity.

In certain embodiments, the valve deployment mechanism includes a plurality of movable fasteners associated therewith which are movable to at least two states: a disengaged state wherein said plurality of fasteners are retracted; and an engaged state wherein said plurality of fasteners are extended. A non-limiting list of fasteners include, but are not limited to, hooks, claws, pins, mesh, etc. that are capable of penetrating tissue or compressing up against tissue at a target surgical site. In an alternative embodiment, the fixation occurs via radial expansion of a structural member without necessarily inserting or penetrating a structure into the tissue.

The plurality of fasteners are typically associated with annular ring assembly having a first annular ring member onto which the plurality of fasteners are connected. The connection may be static (e.g. anchored) or may include a pivot point on the first annular ring member. The conversion from a disengage state to an engaged state may occur, according to one specific embodiment, by rotational movement of the first annular ring member. When the annular ring member is rotated the fasteners catch on the surrounding tissue at the target surgical site and penetrate into the tissue as the annular ring member is further rotated. In this context, the engagement of the fasteners into the tissue is passive, i.e., an indirect result of the rotation of the annular member. In an alternative embodiment, the association between the plurality of fasteners and the remainder of the valve deployment mechanism is configured to enable a more active engagement of the fasteners with the surrounding tissue. An example of this would include a mechanical configuration that involves individually and actively pivoting or projecting out each of the individual fasteners from a retracted state.

In yet a further embodiment, the valve deployment mechanism includes an additional state for the fasteners: a deployed state where the fasteners are rigidly locked into place. In another specific embodiment, the fasteners are irreversibly locked into place once the deployed state is effectuated. According to an even more specific example, the ring assembly includes a second annular ring member that at least partially houses the first annular ring member. The second annular ring member includes a series of windows through which the individual fasteners pass. The series of windows are configured to allow the fasteners to bend or pivot out into an extended position. The series of windows also may possess a groove or notch. The second annular ring member may slide in a perpendicular or oblique direction which shifts the second annular ring member relative to the first annular ring member such that the individual fasteners are forced into the grooves thereby locking the fasteners in place.

According to an additional embodiment, the valve deployment mechanism further includes a first radially expandable member positioned superiorly to the plurality of fasteners. The embodiment may further include a second radially expandable member positioned inferiorly to the plurality of fasteners. These first and second radial expandable members provide further support and securement of the valve at the target surgical site. In conjunction with the deployment of the plurality of fasteners, the first and second radially expandable members expand from a contracted state to an expanded state where they abut up against and push into the tissue at the target surgical site.

In a specific embodiment, the first and/or second radially expandable members are first and second skirt members, respectively. The first and second skirt members may include a series of overlapping segments that swing from an overlapped state to a spread state. The series of segments are shaped and oriented such that when they swing to a spread state, the circumference of the skirt member and increases, thereby resulting in radial expansion of the skirt member. Those skilled in the art will appreciate in view of the teachings herein other structural/mechanical arrangements of radially expandable members. For example, the radial expandable member may comprise a series of curved tubes having different diameters where some of the tubes are inserted into others to form a ring-like shape. During radial expansion, the inserted tubes are urged out of the casing tubes where the overall circumference or diameter of the radially expandable member increases.

The terms "proximal" and "distal" as used in describing an end of a feature of an embodiment of the invention is a modifier referring to the perspective of the user. Thus, a distal end refers to an end of feature that is away from the user and the proximal end refers to the end that is toward the user when the embodiment is in operation.

According to another embodiment, the invention pertains to a heart valve deployment kit for use with a sutureless heart valve. The deployment kit may include a deployment apparatus comprising an elongated conduit having a distal end and a proximal end, a linkage that is matable with the heart valve at the distal end; and a control unit disposed at or proximate to said proximal end relative to said distal end. The control unit includes one or more actuators to control the states of the deployment mechanism, and in particular the state of the plurality of fasteners and the first and/or second skirt members. The control unit may also include an actuator to control release of the deployment apparatus from the sutureless heart valve. The one or more actuators may be combined or separate. According to a specific embodiment, the control unit includes a first actuator for translating said plurality of fasteners to and from a disengaged and engaged state; a second actuator for commuting radial expansion of said first and/or second skirt members; and a deployment actuator for effectuating said plurality fasteners into a deployed state.

In yet a further embodiment, the invention pertains to a cannula assembly useful in performing heart surgery. The cannula assembly includes a cannula to assist in performing heart surgery at a target surgical area. The cannula assembly may further an inflatable balloon associated with a distal end of the cannula. The inflatable balloon is typically connected to a pump via a tube associated with the cannula. The cannula assembly may further include a second conduit associated with the cannula and which includes a port that is in continuity with the target surgical site and obstructed to the downstream aorta by the inflatable balloon when the balloon is secured in the subject.

According to another embodiment, the invention is directed to a method of repairing or replacing a heart valve at a target surgical site with a sutureless heart valve. The method involves positioning the sutureless heart valve at a first position at the target surgical site, where the positioning is executed with the valve deployment mechanism in a disengaged state. The method further involves actuating the sutureless heart valve into an engaged state at the first position. If the surgeon, upon evaluating the securement of the valve is unsatisfied with it, the sutureless heart valve is returned to a disengaged state and repositioned. Upon repositioning, the sutureless heart valve is actuated to an engaged state again. This process of positioning, engaging, disengaging, repositioning, reengaging can occur or multiple times depending on the surgeons analysis of the securement at the target surgical site. Upon the sutureless valve being secured and positioned to the surgeons satisfaction, the sutureless valve is deployed, which involves urging the plurality of the fasteners into a deployed state. In a more specific embodiment, deployment includes deploying the plurality of fasteners and radially expanding the radially expandable members.

The steps of the method embodiments may be conducted with a deployment apparatus as described above. The target surgical site may be the area around an aortic or mitral valve. The method may involve first resecting out the native valve or alternatively, trimming the valve and securing the sutureless heart valve over the existing valve.

According to another embodiment, sutureless heart valve includes a housing with a valve support member surrounding the surface of the valve component. Based on the teachings herein, one skilled in the art will devise appropriate materials for manufacture of the valve support member. In one example, there is a valve support member between the ring assembly and the superior radially expandable member and a second valve support member positioned between the ring assembly and the inferiorly positioned radially expandable member. The valve support members made be made of known suitable materials, including but not limited to, Dacron™. The radially expandable members made be made of a thermoplastic material such as, but not limited, Nitinol or deformable plastic. The fasteners may be made of a suitably rigid material, including but not limited to, rigid plastics and/or metals. In a specific embodiment, the fasteners are made of titanium. It should borne in mind that the number, size, and shape of the fasteners, may of course, vary. Generally the number, size, and shape may be configured to ensure adequate attachment or fixation while minimizing damage to surrounding tissue that may be caused by repeatedly extending and retracting of the rings into the surrounding tissue during deployment and un-deployment. The fasteners may also be of limited length (e.g., less than 3 mm) so that eventual valve replacement or removal at the end of the valve's life (e.g., in 20 years) will not require excessive removal of tissue.

Figure 1:
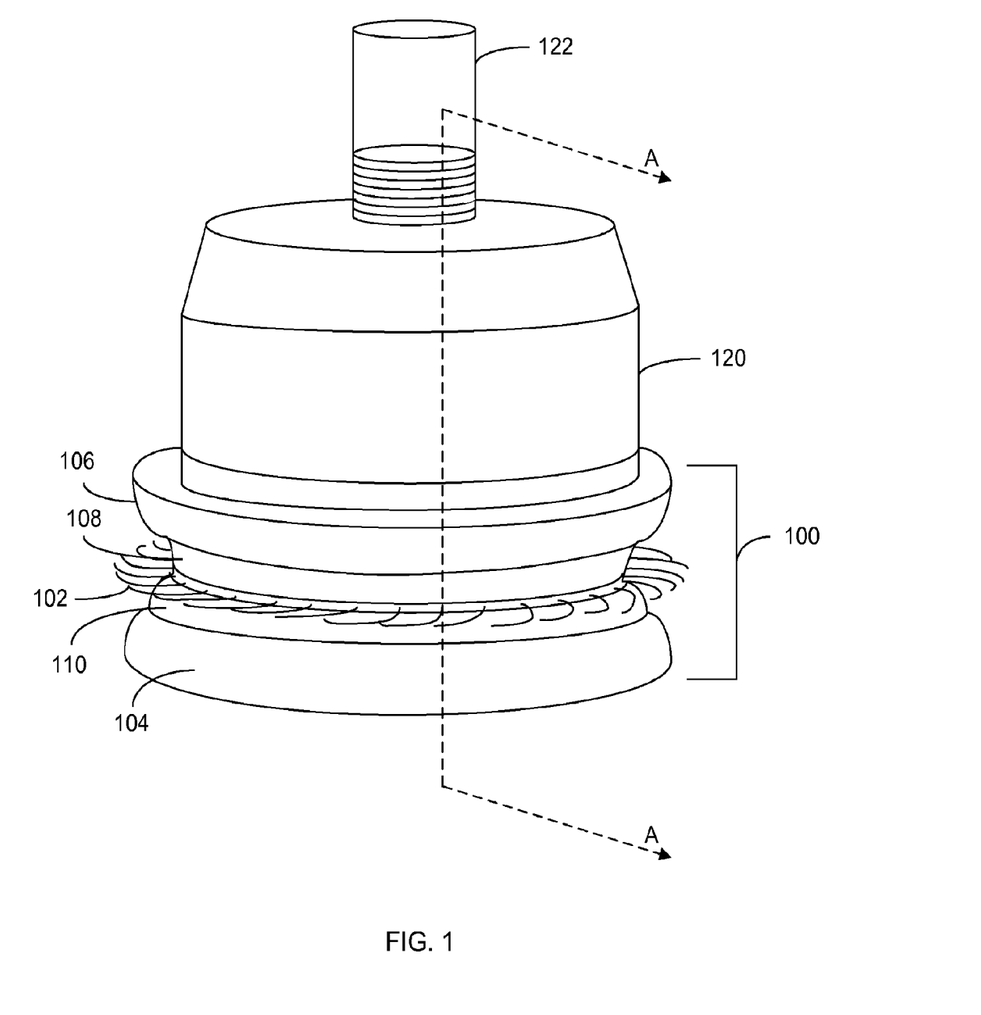
FIG. 1 shows a side view of a sutureless heart valve embodiment associated with a portion of a deployment apparatus embodiment.

Turning to the drawings, FIG. 1 shows one embodiment of the invention that shows a side, slightly top perspective of a sutureless valve 90 mated to a linkage encasement 120. The valve 90 includes a series of fasteners 102 that are associated with a first annular member (not shown) and extend out from the valve 90. Positioned immediately superiorly and inferiorly to the fasteners 102 is a first and second valve support member 108, 110, respectively. Positioned immediately inferiorly and superiorly to the first and second valve support members 108, 110 are an inferior radially expandable member 104 and superior radially expandable member 106. The linkage encasement 120 is connected to a distal end of an elongated conduit 122. The features 102, 104, 106, 108, and 110 make up a portion of a valve deployment mechanism 100.

Figure 2:
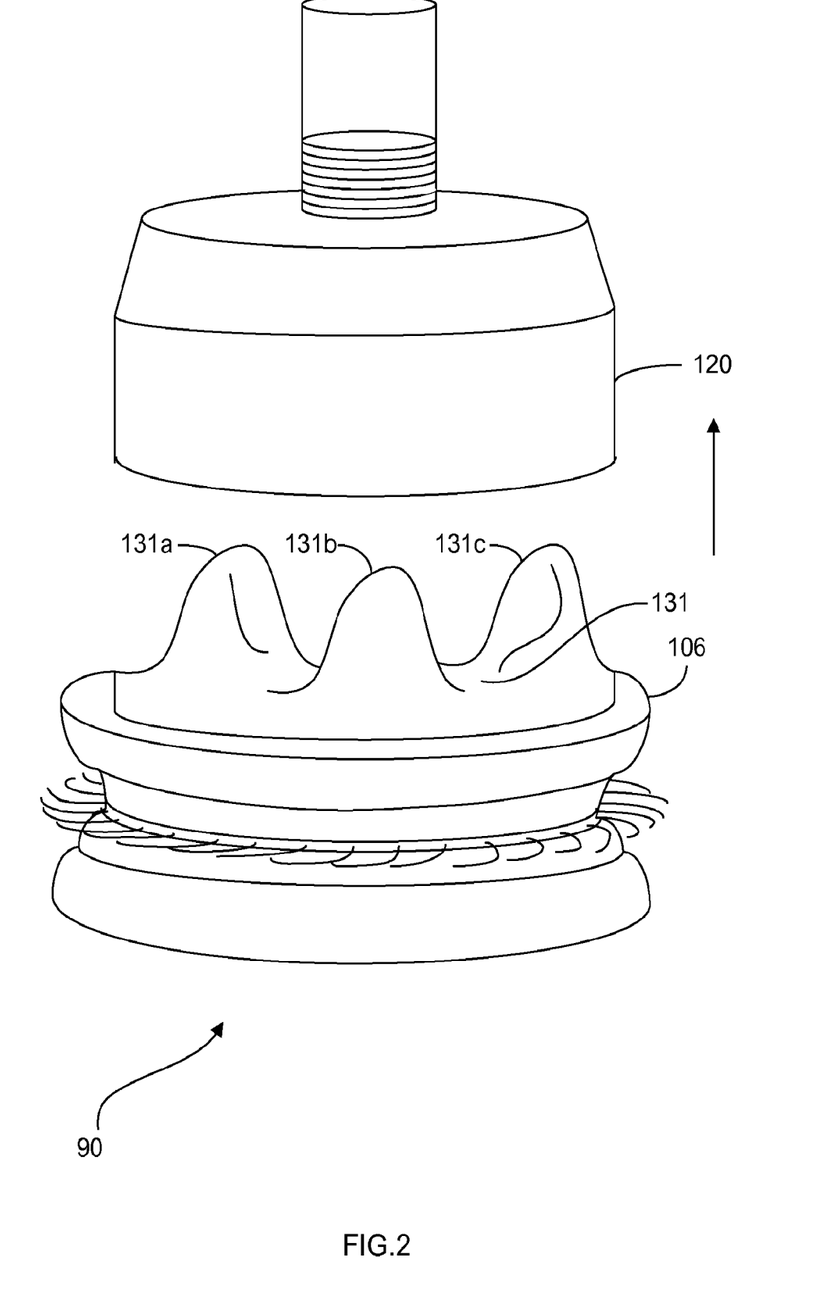
FIG. 2 shows a side view of the embodiment shown in FIG. 1 with the deployment apparatus dissociated with the sutureless heart valve embodiment.

FIG. 2 shows the valve 90 and linkage encasement 120 shown in FIG. 1, with the valve 100 release from the linkage encasement 120. The removal of the linkage encasement reveals the valve component 131, which has three cusps 131a-b. Also shown is the superior radially expandable member outwardly associated with the valve component 131.

Figure 3:
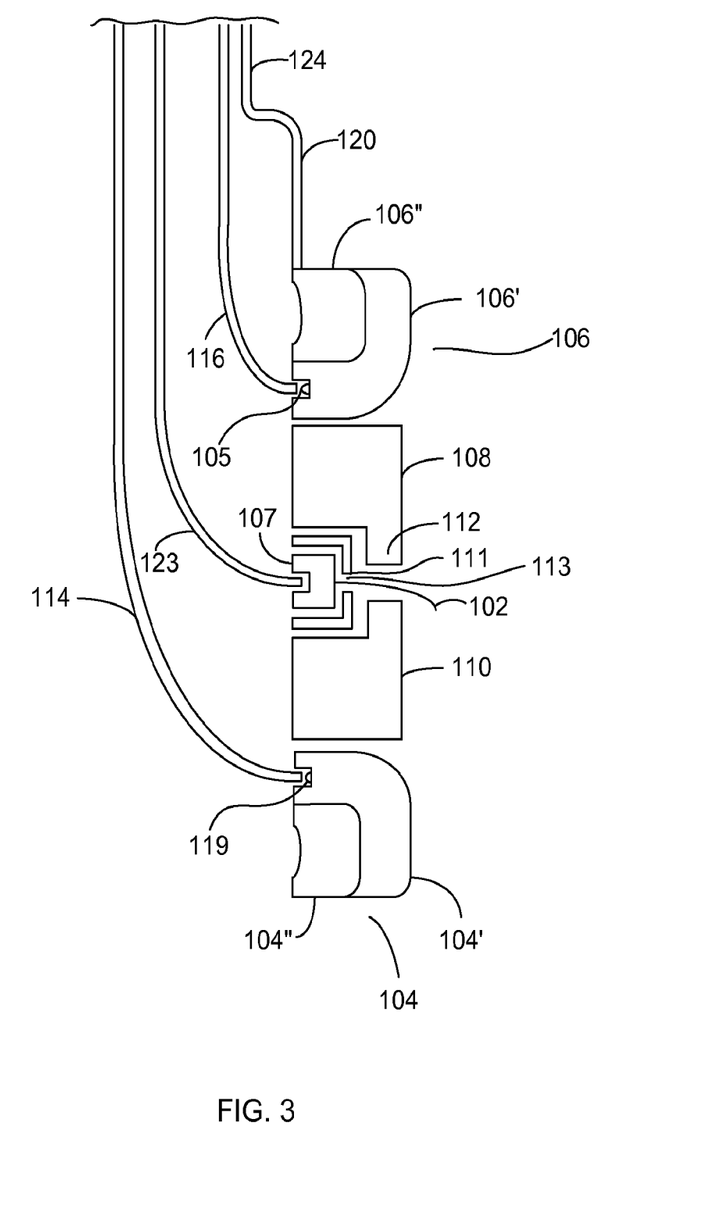
FIG. 3 shows a cross-sectional view of along axis A-A in FIG. 1.

FIG. 3 shows a cross-sectional view of the edge of the valve 90 and linkage encasement 120 along the axis A-A designated by dashed lines in FIG. 1. FIG. 3 shows one example of a structural interaction with various components of the valve deployment mechanism 100 with components of the deployment apparatus that execute the deployment of the valve 90 at a target surgical site. As shown, the fasteners 102 are associated with a first annular ring member 107. The first annular ring member 107 is at least partially housed by a second annular ring member 111. The second annular ring member 111 defines a window 113 through which the fastener 102 passes. Also seen are the superior and inferior valve support components 108, 110. The radially expandable members 106 and 104 are made up of a series of overlapping segments 106' and 106", and 104' and 104", respectively. Segment 106' pivots about pivot point 105 and Segment 104' pivots about pivot point 119. A first linker 114 interacts with segment 104' proximate to pivot point 119. A second linker 116 interacts with segment 106' at pivot point 105. Urging from the first and second linkers 114 and 116, respectively, causes movement of the segments 104' and 106' respectively. As shown this movement is a pivoting that results in displacement of the segments 104' and 106' relative to segments 104" and 106", respectively. Also shown is linker 123 that interacts with the first annular ring member 107. Rotation of the annular ring member 107 is urged by the linker 123 via control at a location on the deployment apparatus (see FIG. 4, 150 for example) outside the target surgical area. Once the valve is positioned to the satisfaction of the surgeon, the plurality of fasteners are locked into place (deployed) and the radially expandable members are also locked. The deployment apparatus is then disconnected to the valve.

The linkers 114, 116, 123 may be wires, cables or similar structure that are moved at a location outside the target surgical site. It should be pointed out that the control of the functionality of the valve deployment mechanism 100 can comprise numerous different versions. What is important is the general function of the valve deployment mechanism and the concept of controlling this function at a site proximal to the operator outside the surgical site. One example of controlling this function is further described below.

Figure 4:
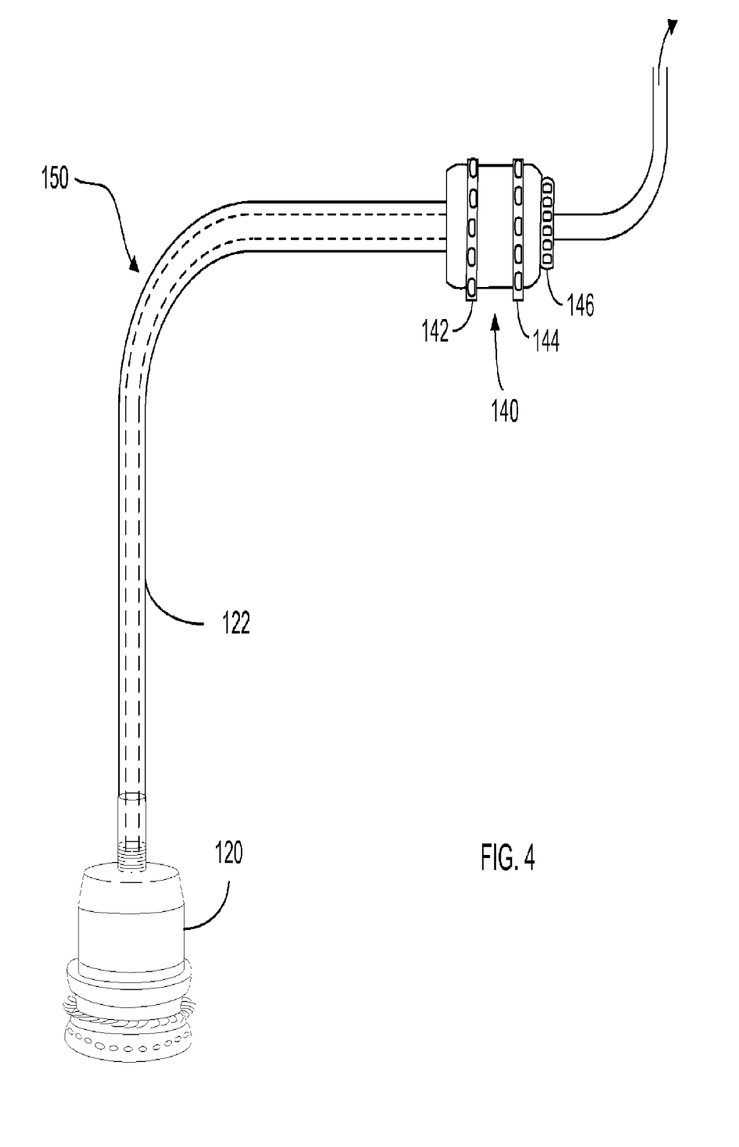
FIG. 4 shows a side view of a heart valve deployment apparatus embodiment.

FIG. 4 shows a side view of a deployment apparatus 150 that may be used to deploy a sutureless valve 90 at a target surgical area. The deployment apparatus 150 includes an elongated conduit 122 having a distal end and a proximal end. The linkage 120 is shown at the distal end. Positioned on the elongated conduit 122 is a control unit 140. The control unit 140 comprises actuators for controlling the functionality of the valve deployment mechanism. In the version shown, the control unit 140 comprises a first dial 142 that controls the expansion states of the radially expandable members. Rotation movement causes radially expansion of such members. The second dial 144 controls the engagement states of the plurality of fasteners. The third dial 146 controls the locking of the plurality of the fasteners and the radially expandable members and controls release of the sutureless valve 90.

Figure 5A:
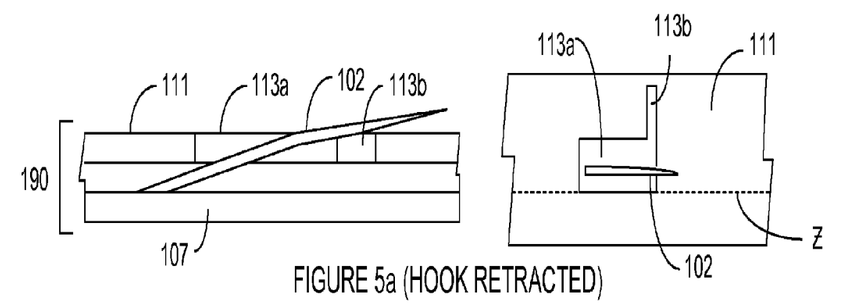
Figure 5B:
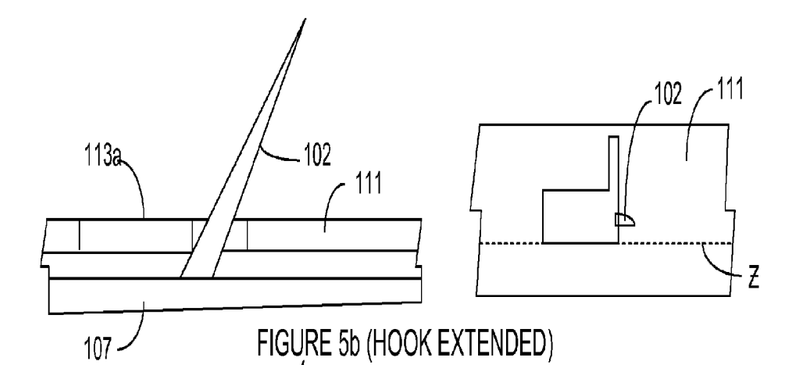
Figure 5C:
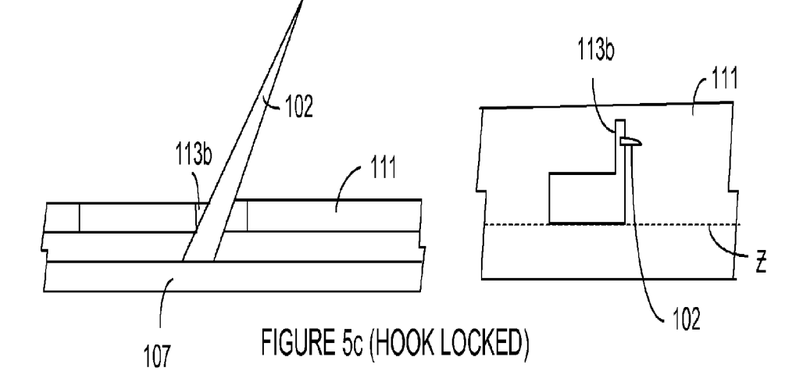
Figure 9:
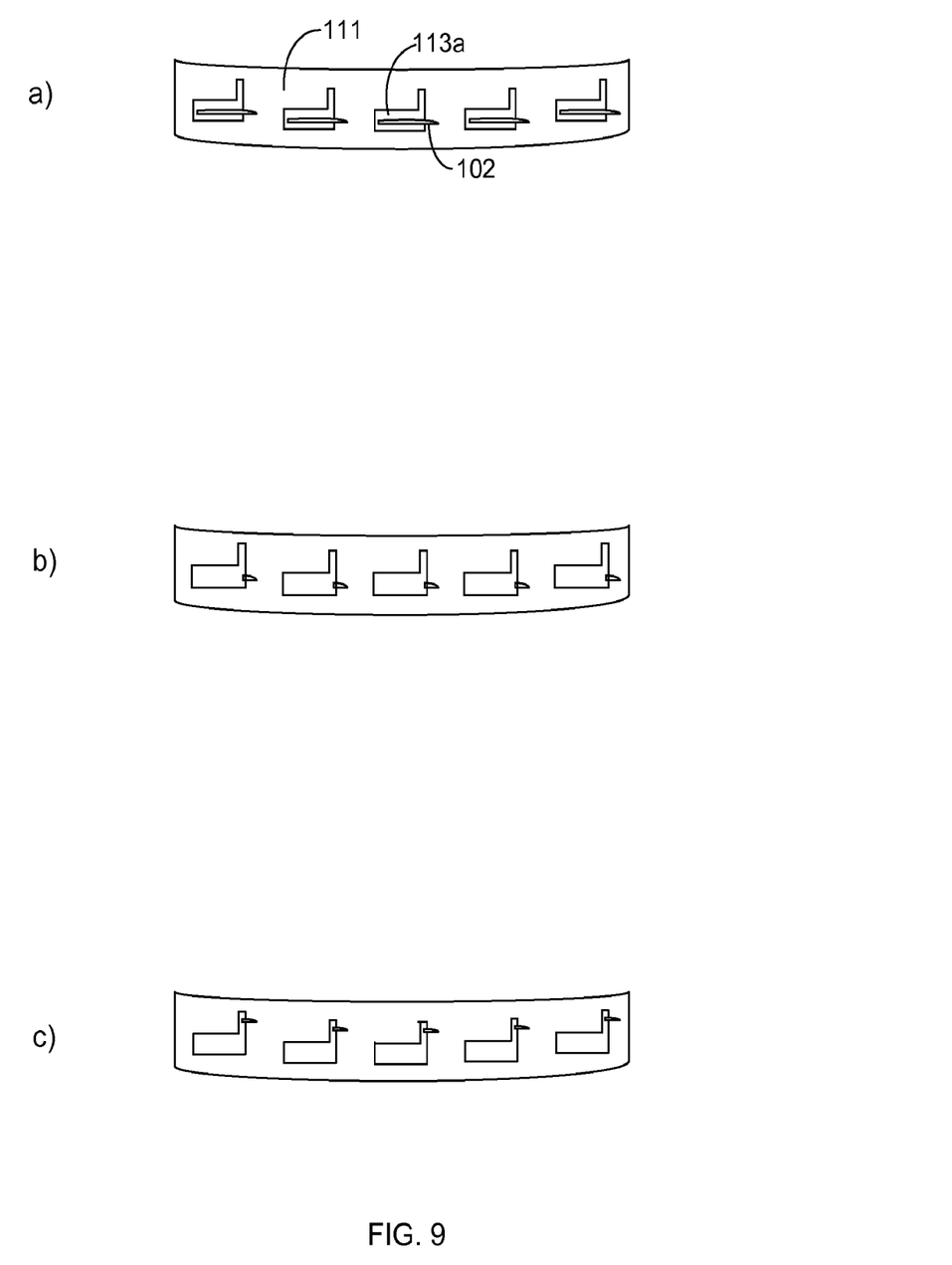

FIG. 5 shows a side view close up (right column) and cross-sectional view (left column) of a ring assembly 190. The cross-sectional view is depicted along axis z. FIG. 5a shows the ring assembly 190 in a retracted state where the fastener 102 is retracted. In the version shown in FIG. 5a the fastener 102 is a prong which minimally perches out of the window 113a and lies close along second annular ring member 111. FIG. 5b shows the ring assembly 190 in an extended state where the fastener 102 is extended out from the second annular ring member 111 and is extending out from window 113a. Converting from the retracted state to the extended state involves rotational movement of the first annular ring member 107 relative to the second annular ring member 111. FIG. 5c shows the ring assembly in a deployed state where the second annular ring member 111 is shifted relative to the first annular ring member 107 such that the fastener 102 is pushed into window 113b. FIG. 9 provides a full side view of the second annular ring member and fastener in a retracted state (FIG. 9a), extended state (FIG. 9b) and deployed state (FIG. 9c).

Figure 6:
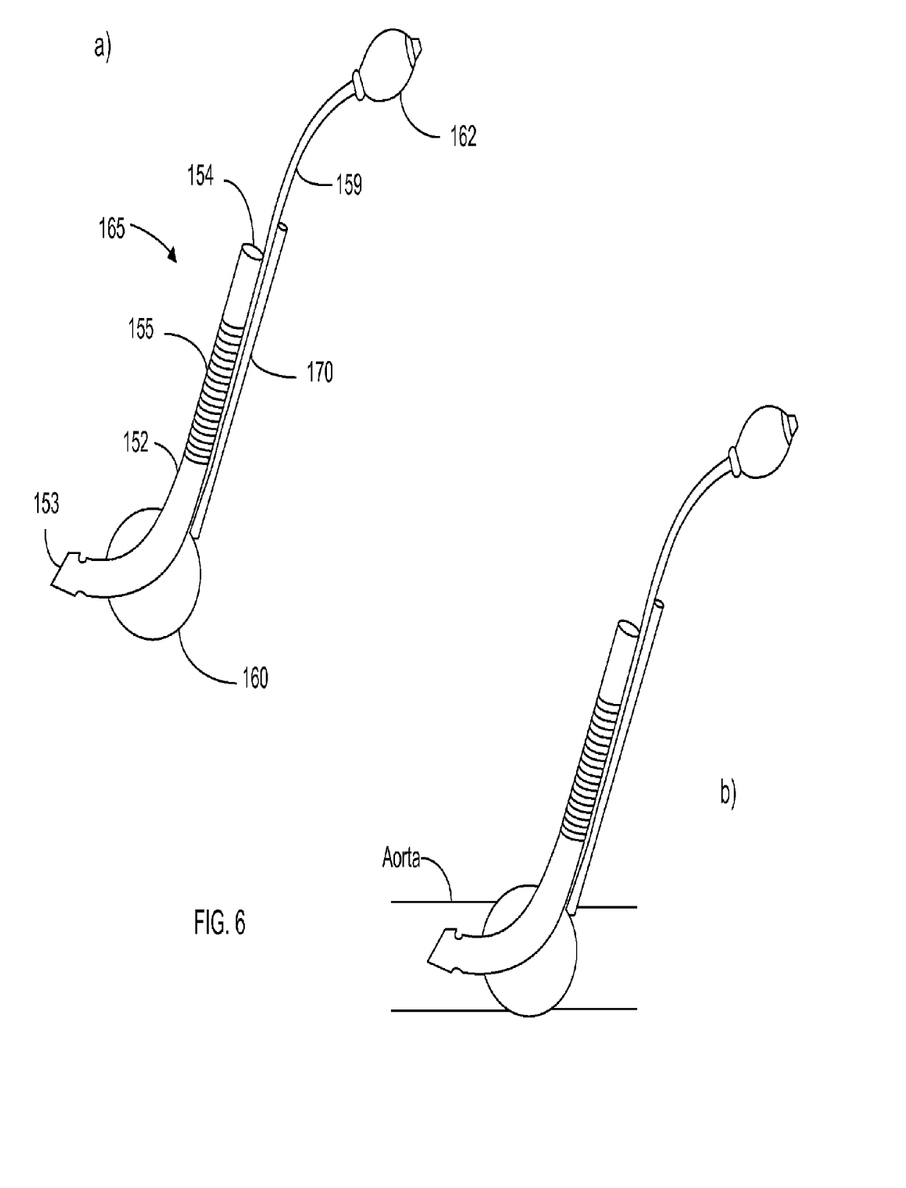
FIG. 6 shows a side view of a cannula assembly embodiment useful in conjunction with performing heart valve replacement surgery with heart valve embodiments.

FIG. 6 shows a side view of cannula assembly 165 useful for conducting heart valve replacement or repair surgery. The cannula assembly 165 includes an elongated cannula 152 having a distal end 153 and a proximal end 154. The cannula 152 as shown further includes a wire network 155 to prevent the cannula 152 from collapsing. Positioned toward the distal end 153 is an inflatable balloon component 160 associated with the cannula. The inflatable balloon allows for occlusion and anchoring of the cannula assembly in luminal space such as vasculature near the target surgical site. The balloon component 160 is connected to a pump component 162 via a tube 159. Associated with the cannula is a second cannula 170 that is configured so as to open at a region in continuity with the target surgical site where the downstream aorta is occluded by the inflatable balloon (see FIG. 6b).

The cannula assembly embodiment 150 provides a balloon occluder 160 or clamp with a second cannula 170 that provides a cardioplegia port and a suction port. Such a combined instrument may reduce the number of instruments required and thus may require smaller or fewer incisions. Such a combined device may provide an occluder or a clamp, with a cannula for the heart/lung machine, providing a port for cardioplegia to stop the heart and suction for de-airing. One advantage of such a cannula system in the exemplary context of aortic valve surgery is that, once the surgeon begins to close the aorta, the surgeon can use suction to capture any air that is coming out of the ventricle. The surgeon can then let the balloon down and take the device out and come off bypass.

Figure 7A:
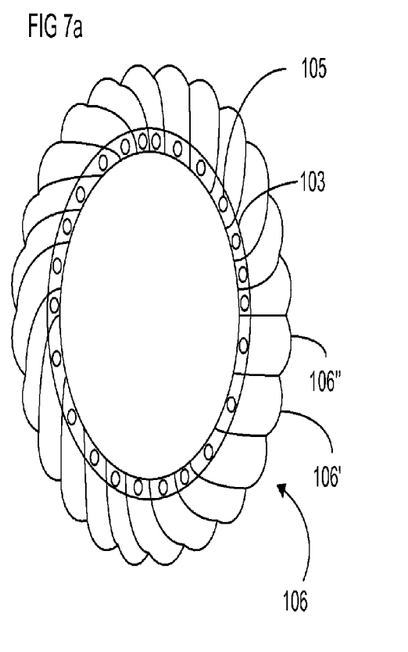
Figure 7B:
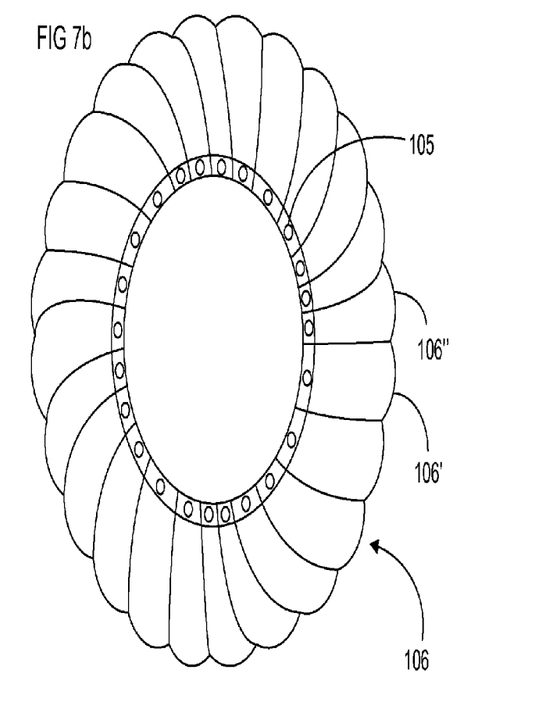
Figure 8A:
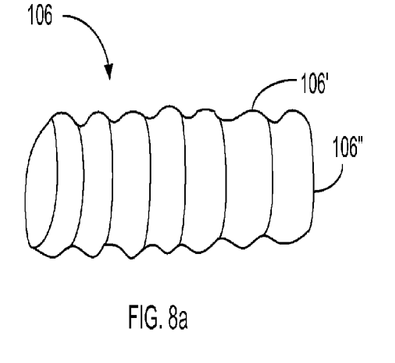
Figure 8B:
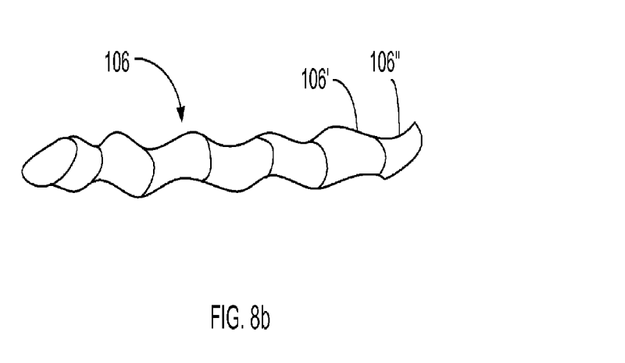

FIG. 7 shows a top view of a radially expandable member embodiment 106. The radially expandable member is shown in a contracted state (FIG. 7a) and an expanded state (FIG. 7b.) FIG. 8 shows a side view of the radially expandable member 106 in contracted state (FIG. 8a) and an expanded state (FIG. 8b). The radially expandable member is comprised of segments that pivot about pivot point 105. As shown, the pivot point 105 is a pin that rides on a track 103. In the contracted state, the segments are pivoted inward where more surface area of the segments overlap, as illustrated by segments 106' and 106". In the expanded state, the segments swing outward where more surface area is exposed and their longer longitudinal axis points in a more outward direction (see segments 106' and 106"). FIG. 8 shows how according to this illustrated embodiment, the segments actually swing outwardly and downwardly to increase the diameter of the radially expanding member 106.

Figure 10:
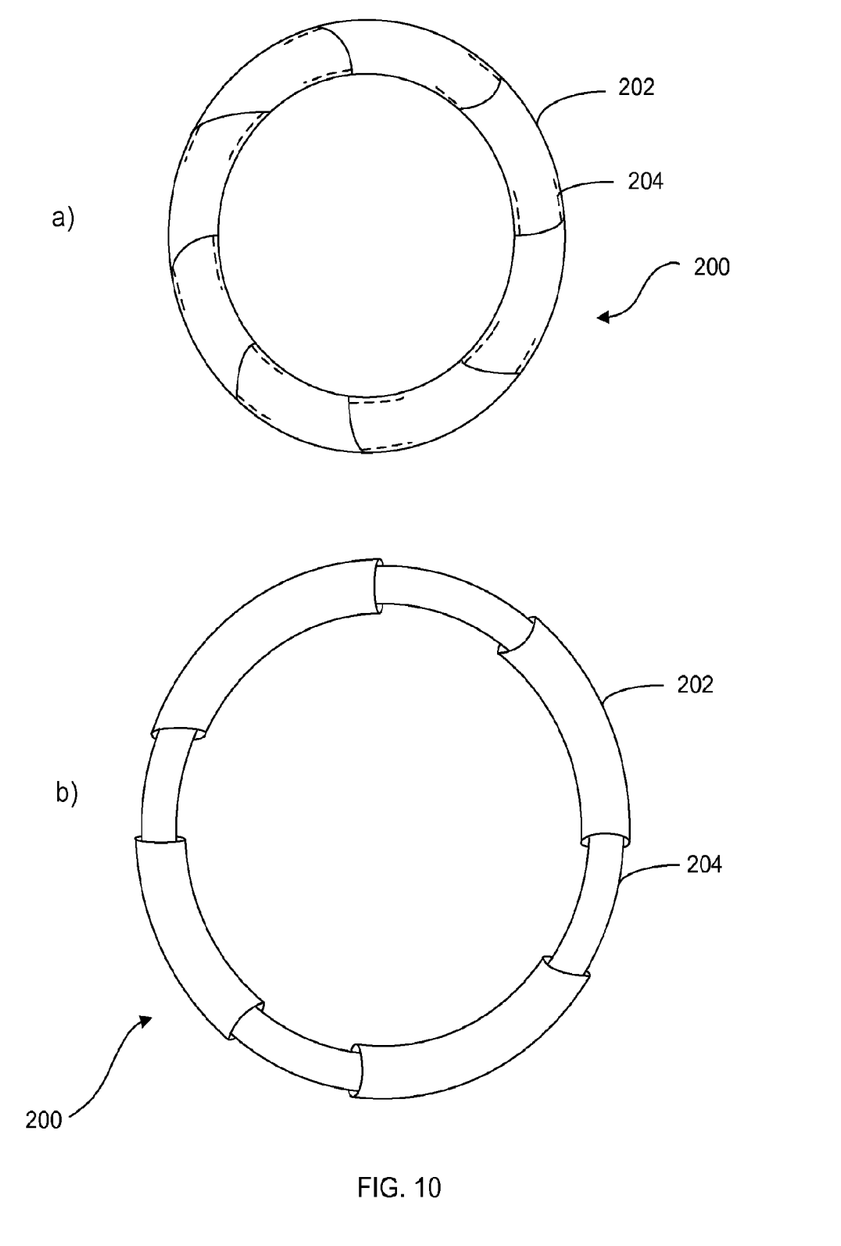
FIG. 10 shows another embodiment of a radially expandable member for use with a heart valve embodiment. The radially expandable member is shown in a contracted state (FIG. 10a) and an expanded state (FIG. 10b).

FIG. 10 shows an alternative embodiment of a radially expandable member 200 that may be used with a valve deployment mechanism described herein. The member 200 comprises a series of outer tubes 202 and inner tubes 204. In a contracted state shown in FIG. 10a, the inner tubes 204 a predominantly inserted into the outer tubes 202. In the expanded state, radial expansion of the member 200 is urged whereby the outer tubes 202 slide apart to expose the inner tubes 204. This sliding increases the diameter (or outer circumference) of the member 200.

Figure 11:
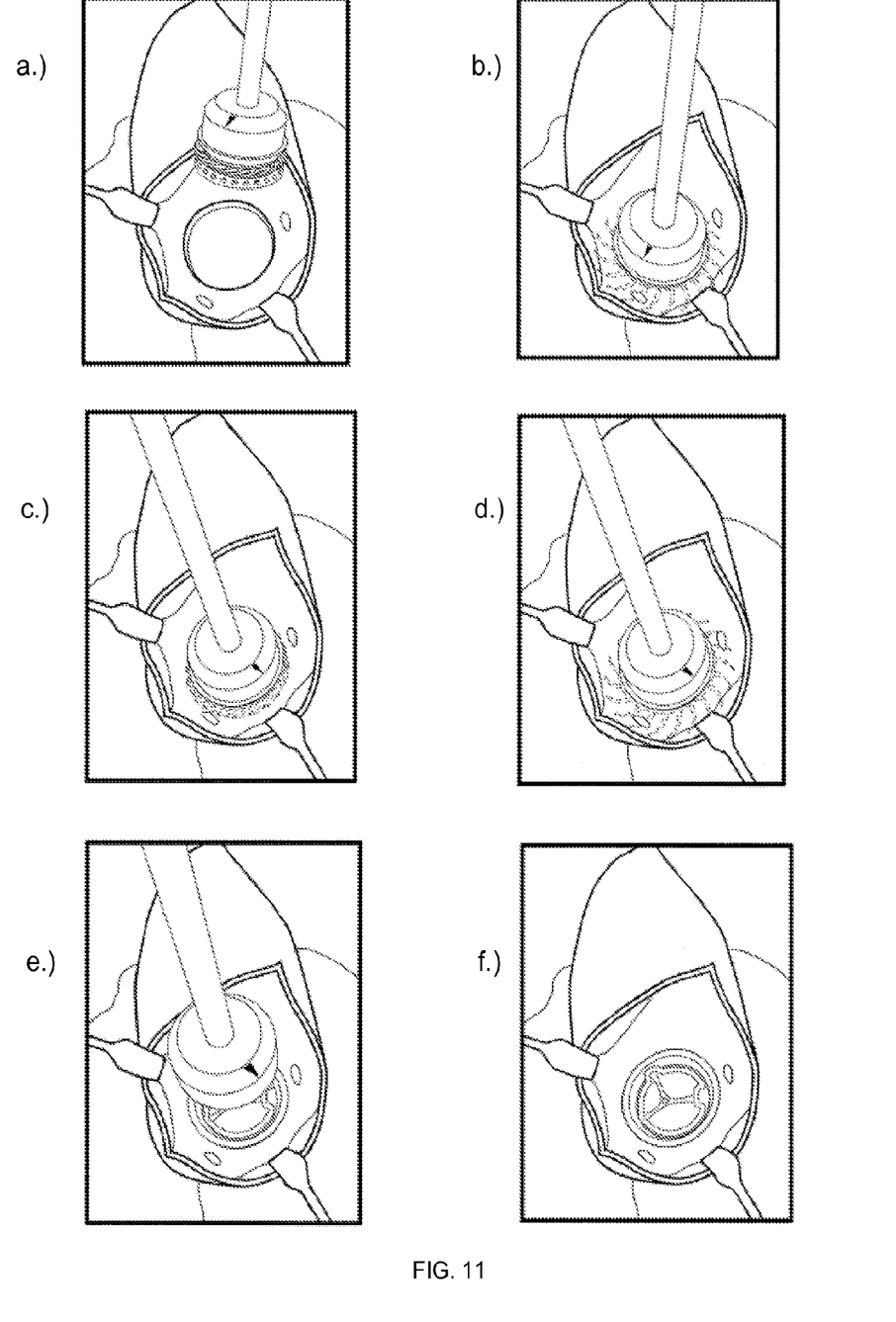

FIG. 11 shows a sequential depiction of a method embodiment involving deployment of a sutureless heart valve using a deployment apparatus. In FIG. 11a, a native aortic valve has been removed leaving an annulus for securement of the sutureless heart valve. In FIG. 11b, the sutureless heart valve has been positioned in the annulus and the fasteners have been extended in their engaged state. In FIG. 11c, the fasteners have been retracted and the sutureless heart valve has been repositioned. FIG. 11d shows the fasteners extended with valve in its engaged state at the new position. FIG. 11e shows the release of the sutureless valve from the deployment apparatus after deployment of the fasteners. FIG. 11f shows the sutureless valve finally deployed at the annulus.

After extending the fasteners to temporarily engage the valve, the surgeon can then visually, or using an instrument such as forceps, inspect the valve's position and seating to check for gaps, holes, calcification, or other problems. Through such inspection, the surgeon may realize that the valve is not the appropriate size or that the annulus is not sufficiently cylindrical, for example, because further decalcification is required.

In an exemplary surgical procedure, a surgeon may recognize that resizing, further decalcification, or other adjustment is required because the surgeon can see some or all of the fasteners s extending from the valve indicating that such fasteners are not properly seated within tissue and thus that adjustments may be required. Similarly, even if such a visual inspection does not reveal a problem, the surgeon may identify that an adjustment is required using a surgical instrument such as forceps. The surgeon may gently test for gaps or other areas around the valve by pushing with the end of the forceps, moving the forceps around the perimeter to feel any areas where the forceps can go through, or otherwise use a surgical instrument to feel for issues. If adjustments are required, the surgeon can disengage the valve, adjust the positioning of the valve and reengage the valve.

Once the surgeon is satisfied with the reengaged position of the valve, the deployment apparatus can be used to more permanently deploy the device by locking the rings in their deployed positions and/or activating additional locking/deployment mechanisms such as one or more radially expandable members. The final deployment or locking mechanism may be deployed in either order or together at the same time.

As described above, one material used to make the radially expandable members may include nitinol. This may be particularly suitable since once the nitinol reaches body temperature, it becomes stiff and will act to further secure the valve. After releasing the valve, the surgeon can start suction through the de-airing cannula to replace suction previously provided by the suction/vent of the deployment device. The surgeon can cardiovert the heart and get it started beating, let the balloon down and otherwise complete the procedure.

The exemplary valve and deployment systems described herein are preferably used with a heart-lung machine and under conventional surgery conditions to address the risk of embolization, stroke, and other conditions that may occur. The exemplary valve and deployment device described above could be used with existing supporting devices, for example, using a conventional cannula and a balloon occluder or cross clamp.

Alternatively, as illustrated in FIG. 6, a single instrument may be used that combines a balloon occluder or clamp with a second cannula that provides a cardioplegia port and a suction port. Such a combined instrument may reduce the number of instruments required and thus may require smaller or fewer incisions. Such a combined device may provide an occluder or a clamp, with a cannula for the heart/lung machine, providing a port for cardioplegia to stop the heart and suction for de-airing.

An exemplary cannula system combines a balloon occluder with a cannula that provides a cardioplegia port to provide cardioplegia into the coronary arteries to stop the heart and provides suction. One advantage of such a cannula system in the exemplary context of aortic valve surgery is that, once the surgeon begins to close the aorta, the surgeon can use suction to capture any air that is coming out of the ventricle. The surgeon can then let the balloon down and take the device out and come off bypass. Such a cannula system can be wire bound.

Valves and valve deployment systems that use one or more of the features disclosed herein may provide many or all of the advantages of minimally invasive procedures, but still have comparable effectiveness, efficacy, reduced risk, and quality to existing suture-based open procedures. Accordingly, various aspects of the exemplary valve and deployment devices described herein provide various advantages over existing percutaneous suture-less valves. For example, surgical imaging required for catheter-based valve delivery systems may be reduced or eliminated in embodiments in which the valve is installed through one or more small incisions through which the valve's placement can be confirmed visually and through the use of instruments used through the incisions.

In addition, the ability to deploy and undeploy the valve may improve placement and help reduce the occurrence of perivalvular leaks. The use of a hook-type deployment mechanism can also help reduce such perivalvular leaks. Moreover, the risk of leaks can be further reduced by providing multiple securing mechanisms, e.g., both a hook-type and a nitinol-based mechanism, to hold a valve in place. Such perivalvular leaks, which can cause various risks including hemolysis, ongoing aortic insufficiency and ongoing decompensation, may be a more substantial risk with existing percutaneous suture-less valves occurring in a substantially higher percentage of cases.

The risk of such percutaneous leaks with valves and valve deployment systems that employ the features and techniques disclosed herein may reduce the risk of such leaks to levels similar to, or perhaps even better than, the risk of such leaks in existing suture-based, open valve replacement procedures, perhaps reducing such risk to 1% of patients or even less. However, unlike such open procedures, valves and valve deployment systems disclosed herein can generally be used with smaller incision surgical techniques, e.g., using minimally invasive surgical techniques as opposed sternotomy-based or other open surgical techniques.

The smaller incision and other minimally invasive surgical techniques can reduce surgical risks, shorten recovery time, and provide other benefits over open surgery. An additional possible advantage over conventional suture-based deployment systems is that the absence of the sutures may allow a larger-sized valve to be used than would be used in the context of suture-based deployment. Certain embodiments disclosed herein provide valves and valve deployment system features that avoid subvalvular componative tissue. The variance may be a lot lower that in suture-based valve deployment.

A possible additional advantage over conventional suture-based deployment systems is that the surgical technique used with valves and valve deployment systems disclosed herein may be less complicated and easier for surgeons, especially those surgeons who are not valve specialists. The surgery may also be quicker.

Valve surgery using the valves and valve deployment systems disclosed herein may be a more attractive option to potential patients than valve surgery involving open surgery, for example, because of the reduced recovery time, pain, and risk of infection. Such patients may be more willing to submit to surgery at an earlier stage of stenosis allowing surgeons to better treat the condition and avoiding or reducing the risk that a patient will die or suffer other heart problems during a period in which the patient has put off the surgery. Stenosis may be addressed more commonly before the amount of stenosis becomes critical or threatens the patient's life.

None of the features disclosed in the above examples should be considered essential. For example, an alternative valve design would not use a radially expandable members such as a nitinol skirt. As another example, the exemplary hook-based deployment mechanism described above could be omitted or replaced with another type of mechanical-based controllable attachment mechanism that can be deployed and un-deployed during the surgical procedure. As another example of feature modifications, while certain embodiments provide a valve that is deployed without sutures, sutures may be optionally used with such a "sutureless" valve for further support if deemed necessary. For example, a surgery may involve an odd-shaped annulus to which hook-type mechanisms are not adequately fixating in one or more problem areas. A surgeon may put in one or more sutures to help secure in the problem areas. In such circumstances, the presence of the two nitinol skirts may also help prevent a leak.

As another example of feature modifications, while certain controls of a deployment device have been described as dials and buttons, such controls could be substituted with other types of controls including, but not limited to, dials, buttons, squeeze mechanisms, augers, triggers, and computer controlled controls. Mechanical interactions between the deployment device controls could also be configured to ensure that the surgeon uses those controls in a certain order. For example, so that the valve cannot be released unless both the hook and skirt dials of the exemplary device described in FIG. 1 are completely turned to their fully-deployed positions.

In an alternative embodiment, the valve deployment mechanism utilizes one or more radially expandable members as the mechanism to secure the sutureless valve into place without necessarily having a member that utilizes fasteners. In other words, the concept of using radially expandable member embodiments as described herein can implemented as the primary or sole basis of the deployment mechanism to secure the heart valve into place. This could be implemented without the fasteners or ring assembly including fasteners as described herein.

As another example of feature modifications, a valve could include an alternative to the nitinol skirts described in the above exemplary embodiments. One or more simple nitinol rings could be used for example. As another example, a non-nitinol ring or even a different valve projection or other feature could be used to cause compression or flattening to fixate the valve.

As yet another example of feature modifications, a valve could include orientation markers to help a surgeon properly position and orient the valve. Generally, while the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject invention.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. The teachings of any reference, including patent documents, are incorporated herein in their entirety to the extent not inconsistent with the teachings in this disclosure.

What is claimed is:

1. A sutureless heart valve for use in heart valve replacement surgery at a target surgical site, the sutureless heart valve comprising
   a valve component that promotes unidirectional blood flow; and
   a valve deployment mechanism outwardly associated with said valve component, said valve deployment mechanism comprising a first annular member onto which a plurality of movable fasteners are associated and movable to at least two states:
   a disengaged state wherein said plurality of fasteners are retracted; and
   an engaged state wherein said plurality of fasteners are extended; wherein the plurality of fasteners move to the engaged state by rotating the first annular member at the target surgical site in a first direction such that the plurality of fasteners catch surrounding, tissue and return to the disengaged state when rotating the first annular member in a second direction opposite to the first direction; and wherein said valve deployment mechanism comprises a deployed state wherein said plurality of fasteners, when extended, are rigidly irreversibly locked such that said heart valve is securely deployed at the target surgical site.

2. The sutureless heart valve of claim 1, wherein said plurality of fasteners comprises a plurality of metal hooks or barbs.

3. The sutureless heart valve of claim 1, wherein said deployment mechanism further comprises a second annular member peripheral to said first annular member and comprising a series of windows through which individual fasteners of said plurality of fasteners project.

4. The sutureless heart valve of claim 1, wherein said valve component comprises three cusps.

5. The sutureless heart valve of claim 4, wherein said three cusps are derived from tissue or an artificial material.

6. The sutureless heart valve of claim 1, wherein said sutureless heart valve is configured and dimensioned for aortic valve replacement.

7. The sutureless heart valve of claim 1, wherein said sutureless heart valve is configured and dimensioned for mitral valve replacement.

8. The sutureless heart valve of claim 1, wherein said deployment mechanism further comprises a first radially expandable member positioned superiorly to said plurality of fasteners.

9. The sutureless heart valve of claim 8, wherein said deployment mechanism further comprises a second radially expandable member positioned inferiorly to said plurality of fasteners.

10. The sutureless heart valve of claim 8, wherein said first radially expandable member is a skirt of segments.

11. The sutureless heart valve of claim 10, wherein said skirt comprises an overlapping series of segments.

12. The sutureless heart valve of claim 11, wherein said overlapping series of segments are pivotably engaged to a ring base.

13. The sutureless heart valve of claim 11, wherein said deployment mechanism actuates said skirt member from a contracted state to a pivoted state, independent to said engaged state of said plurality of fasteners, wherein the pivoted state urges said series of segments in a radial direction.

14. The sutureless heart valve of claim 11, wherein said deployment mechanism actuates said series of segments by rotating said base skirt ring member.

15. A heart valve deployment kit comprising
the sutureless heart valve as recited in claim 1;
a deployment apparatus comprising an elongated conduit having a distal end and a proximal end,
a linkage that is matable with said heart valve, said valve linkage disposed at said distal end; and
a control unit disposed at or proximate to said proximal end relative to said distal end; said control unit comprising a first actuator for translating said plurality of fasteners to and from a disengaged and engaged state; a second actuator for commuting radial expansion of said first and/or second radially expandable members; and a deployment actuator for effectuating said plurality fasteners into the deployed state.

16. A method of repairing or replacing a heart valve at a target surgical site with a sutureless heart valve comprising a valve component having two or more cusps; and a valve deployment mechanism outwardly associated with said valve component, said valve deployment mechanism comprising a first annular member onto which a plurality of movable fasteners are associated and comprising three states: a disengaged state wherein said plurality of fasteners are retracted; an engaged state wherein said plurality of fasteners are extended; and a deployed state wherein said plurality of fasteners are irreversibly locked in an extended position; said method comprising
  (a) positioning said sutureless heart valve at a first position at said target surgical site, said positioning conducted with the valve deployment mechanism in a disengaged state;
  (b) actuating said sutureless heart valve into an engaged state at said first position by rotating the first annular member at the target surgical site in a first direction such that the plurality of fasteners catch surrounding tissue;
  (c) returning said sutureless heart valve into a disengaged state by rotating the first annular member in a second direction opposite to the first direction;
  (d) repositioning said sutureless heart valve to a subsequent position at said target surgical site;
  (e) reactuating said sutureless heart valve into an engaged state following said repositioning; and
  (f) deploying said sutureless heart valve to the deployed state following step (e).

\* \* \* \* \*